US00PP08850P

United States Patent [19]

Zary

[11] Patent Number: Plant 8,850

[45] Date of Patent: Aug. 2, 1994

[54] MINATURE ROSE PLANT NAMED 'JACIMIN'

[75] Inventor: Keith W. Zary, Thousand Oaks, Calif.

[73] Assignee: Bear Creek Gardens, Inc., Medford, Oreg.

[21] Appl. No.: 42,135

[22] Filed: Apr. 2, 1993

[51] Int. Cl.[5] ..... A01H 5/00

[52] U.S. Cl. ..... Plt./8.1

[58] Field of Search ..... Plt. 8.1, 23

*Primary Examiner*—Howard J. Locker

*Attorney, Agent, or Firm*—Klarquist Sparkman Campbell Leigh & Whinston

[57] ABSTRACT

Miniature rose plant having abundant, small, white, hybrid tea-shaped blooms produced in large clusters; deep green, glossy, disease-resistant foliage; dwarf, upright habit of growth; and ease of production from softwood cuttings.

1 Drawing Sheet

The present invention relates to a new and distinct variety of rose plant of the miniature class which was originated by me by crossing the variety Libby U.S. Plant Pat. No. 4,597 with the variety JACjem, U.S. Plant Pat. No. 5,001.

The primary objective of this breeding was to produce a new rose variety having the compact habit and small, well-formed flowers of the female parent combined with the dark green, glossy foliage, disease resistance and profuse flowering of the male parent. The objective was substantially achieved along with other desirable improvements as evidenced by the following unique combination of characteristics which are outstanding in the new variety and which distinguish it from its parents, as well as from all other varieties of which I am aware:

1. Dark green, glossy, disease-resistant foliage;
2. Vigorous, dwarf, upright habit of growth;
3. Flowers borne in large clusters;
4. Small, hybrid tea-shaped white blooms produced in abundance; and
5. Ease of production from softwood cuttings.

Asexual reproduction of this new variety by softwood cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Libby, U.S. Plant Pat. No. 4,597.

*Pollen parent.*—JACjem, U.S. Plant Pat. No. 5,001.

Classification:

*Botanical.*—*Rosa hybrida.*

*Commercial.*—Miniature.

FLOWER

Observations made from specimens grown in a garden environment in Somis, Calif., from February through October, 1992.

Blooming habit: Recurrent.

Bud:

*Size.*—1 inch when the petals start to unfurl.

*Form.*—Short, pointed ovoid.

*Color.*—When sepals first divide, bud color is White Group 155D, sometimes with the bud tip having a pink blush (Red Group 52C). When half blown, the upper and lower sides of the petals are White Group 155D.

*Sepals.*—Color: Green Group 138B. Surface texture: Covered in fine hairs. There are three lightly appendaged sepals. There are two unappendaged sepals with hairy edges.

*Receptacle.*—Color: Green Group 137D. Shape: Funnel. Size: Small ($\frac{1}{4}\times\frac{1}{4}$ inch). Surface: Smooth.

*Peduncle.*—Length: Short (1–$1\frac{1}{4}$ inches). Surface: Smooth. Color: Light green. Strength: Stiff, erect and slender.

Bloom:

*Size.*—Small. Average open size is $1\frac{1}{2}$–2 inches.

*Borne.*—Several together in rounded clusters, generally of 3 to 7 flowers. Basal shoots can carry clusters of as many as 15 flowers.

*Stems.*—Short (6 to 8 inches).

*Form.*—When first open: High centered. Permanence: Flattens, and all petals curl slightly.

*Petalage.*—Number of petals under normal conditions: 20–25.

*Color.*—The upper and reverse sides of the petals are White Group 155D. The base of each petal is Yellow Group 3C. The major color on the upper side is White Group 155D.

*Variegations.*—None.

*Discoloration.*—The general tonality at the end of the first day: no change. At the end of the third day: no change.

*Fragrance.*—Slight.

Petals:

*Texture.*—Thin.

*Shape.*—Oval.

*Form.*—Tips slightly recurved, edges slightly quilled.

*Arrangement.*—Imbricated, with few petaloids in the center.

*Persistence.*—Drop off cleanly.

*Lastingness.*—On the plant: Fair (4–5 days). As a cut flower: Fair (5–6 days).

Reproductive parts:

*Anthers.*—Size: Medium. Quantity: Many. Color: Yellow. Arrangement: Regular around styles, mixed with occasional petaloids.

*Filaments.*—Color: Yellow.

*Pollen.*—Color: Lemon yellow.

*Styles.*—Color: Red.

*Stigmas.*—Color: Greenish white.

Form: Bush.

Growth: Vigorous, dwarf, upright, branching. A mature plant will have a height of 24 to 26 inches and a breadth of 16 to 18 inches.

Foliage:

*Number of leaflets on normal mid-stem leaves.*—5 or 7.

*Size.*—Small (3–3½ inches × 1½ inches).

*Quantity.*—Abundant.

*Color.*—New foliage: Reddish. Old foliage: Dark green (Green Group 139A).

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Smooth, with occasional prickles.

*Stipules.*—Medium, serrated, bearded.

*Disease resistance.*—Resistant to mildew and rust under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Short, hooked downward.

*Color when young.*—Translucent.

Small prickles:

*Quantity.*—On main stalks: None. On laterals: None.

I claim:

1. A new and distinct variety of rose plant of the miniature class, substantially as herein shown and described, characterized particularly as to novelty by the unique combination of its small, white, hybrid tea-shaped blooms produced in abundance; its deep green, glossy, disease-resistant foliage; its vigorous, dwarf, upright habit of growth; its production of flowers in large clusters; and its ease of production from softwood cuttings.

* * * * *

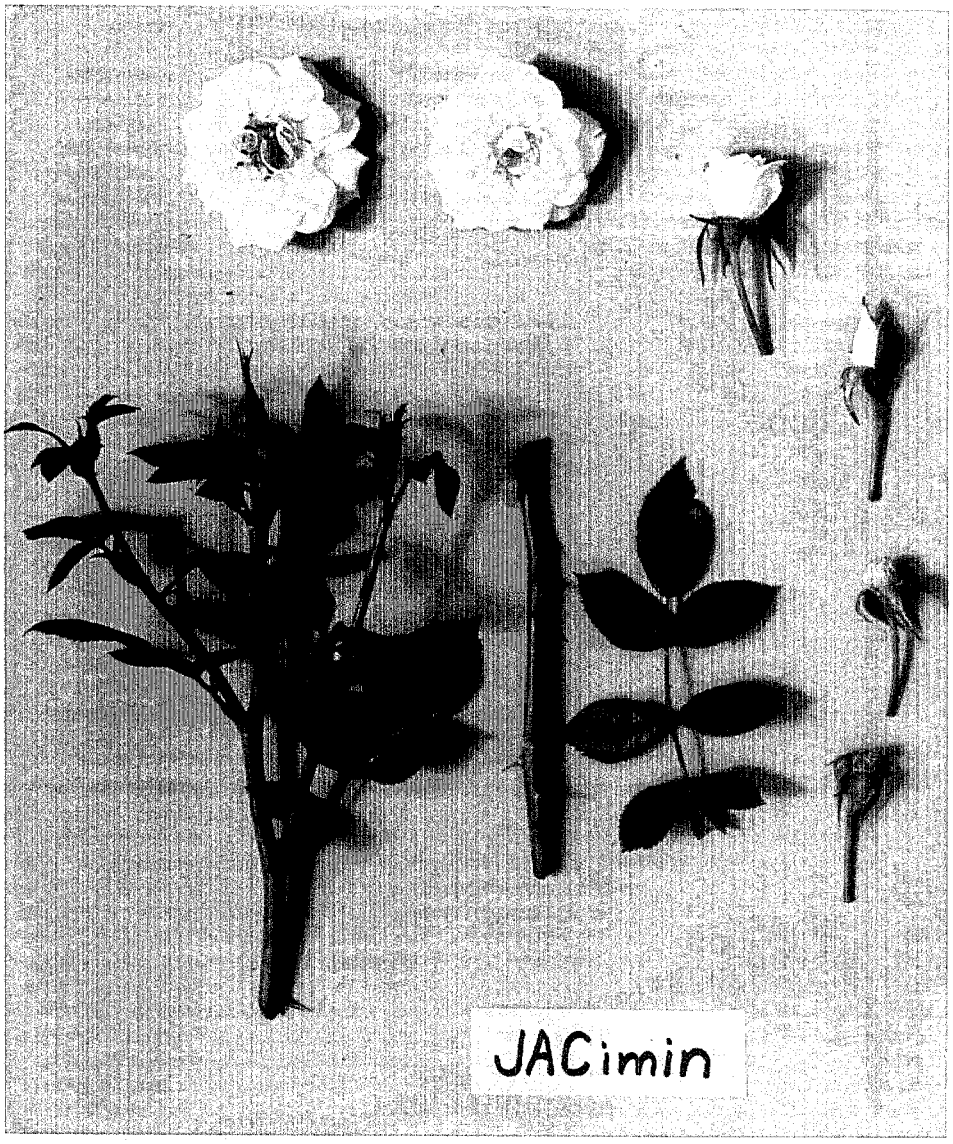
JACimin